United States Patent
Kobayashi et al.

(10) Patent No.: US 10,551,328 B2
(45) Date of Patent: *Feb. 4, 2020

(54) CERAMIC RING TEST DEVICE

(71) Applicant: Applied Materials, Inc., Santa Clara, CA (US)

(72) Inventors: Satoru Kobayashi, Santa Clara, CA (US); Yufei Zhu, Sunnyvale, CA (US); Saurabh Garg, Chicago, IL (US); Soonam Park, Sunnyvale, CA (US); Dmitry Lubomirsky, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 15/817,599

(22) Filed: Nov. 20, 2017

(65) Prior Publication Data

US 2018/0073994 A1     Mar. 15, 2018

Related U.S. Application Data

(63) Continuation of application No. 14/628,733, filed on Feb. 23, 2015, now Pat. No. 9,846,130.

(60) Provisional application No. 61/943,584, filed on Feb. 24, 2014.

(51) Int. Cl.
*G01N 22/00* (2006.01)

(52) U.S. Cl.
CPC .................................. *G01N 22/00* (2013.01)

(58) Field of Classification Search
CPC ...................................................... G01N 22/20
See application file for complete search history.

(56) References Cited

U.S. PATENT DOCUMENTS

| | | | |
|---|---|---|---|
| 5,065,106 A | 11/1991 | Hendrick et al. | |
| 5,874,832 A | 2/1999 | Gabelich | |
| 6,349,670 B1 | 2/2002 | Nakano et al. | |
| 6,859,052 B1 | 2/2005 | Vaucher | |
| 8,519,724 B2 | 8/2013 | Kim et al. | |
| 2003/0006786 A1 | 1/2003 | Kazama et al. | |
| 2004/0061448 A1 | 4/2004 | Avoyan et al. | |
| 2007/0095789 A1 | 5/2007 | Davis et al. | |
| 2008/0238440 A1* | 10/2008 | Yamazawa | G01R 27/02 324/600 |
| 2014/0299152 A1* | 10/2014 | Yoshikawa | C23C 16/511 134/1.1 |

OTHER PUBLICATIONS

International Search Report and Written Opinion dated May 29, 2015, on application No. PCT/US2015/017368.

* cited by examiner

*Primary Examiner* — Minh Q Phan
(74) *Attorney, Agent, or Firm* — Lowenstein Sandler LLP

(57) ABSTRACT

A test fixture includes an outer conductor and an inner conductor disposed within and electrically isolated from the outer conductor. The inner conductor includes a top portion having a first diameter, a bottom portion having a second diameter, and a third portion proximate the bottom portion that has a third diameter that is less than the second diameter and is greater than the first diameter. An electrical property of a chamber component disposed within the outer conductor is measurable based on application of a signal to at least one of the outer conductor or the inner conductor.

20 Claims, 4 Drawing Sheets

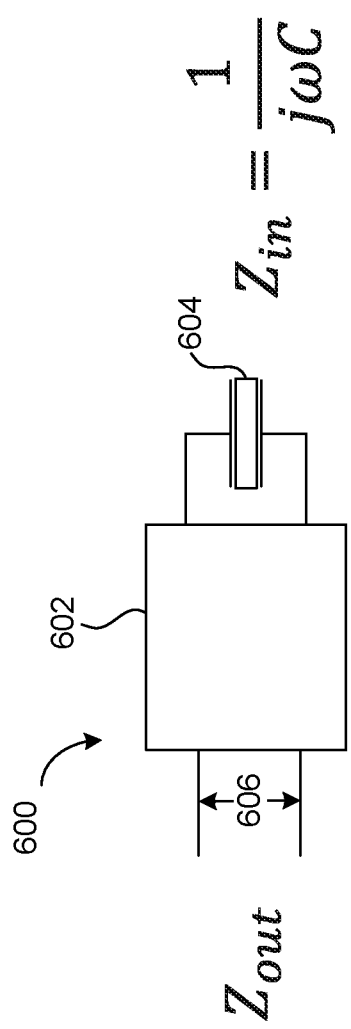
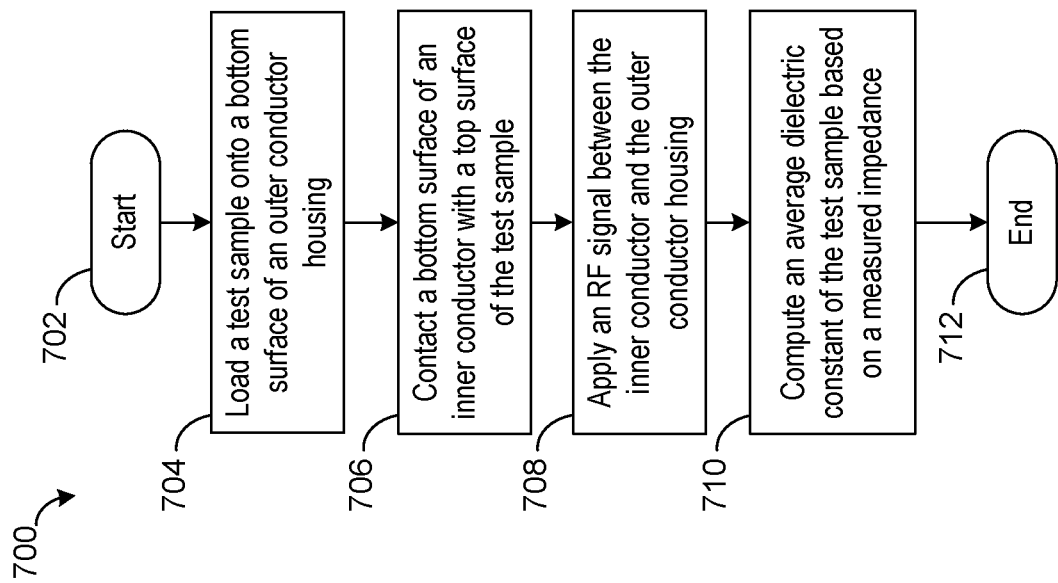

CERAMIC RING TEST DEVICE

CROSS REFERENCE TO RELATED APPLICATION

This application is a continuation application of U.S. patent application Ser. No. 14/628,733, filed Feb. 23, 2015, which claims the benefit of priority of U.S. Provisional Patent Application No. 61/943,584, filed Feb. 24, 2014, the entire contents of both are hereby incorporated by reference.

TECHNICAL FIELD

Embodiments of the present disclosure relate, in general, to a test device for non-destructively measuring the dielectric constant of a test sample, such as a ceramic ring.

BACKGROUND

In the semiconductor industry, plasma processing chambers are used to perform various plasma processing techniques. Such techniques include, for example, low temperature plasma etching, low temperature plasma ashing, and plasma chemical vapor deposition. Some plasma processing chambers include a cylindrical ceramic ring located in between top and bottom electrodes. In such chambers, applied radio-frequency (RF) power is dissipated not only in the plasma but also in the ceramic ring, which may lead to unwanted power dissipation when the dielectric constant and phase delay of the ceramic ring are high.

When a specific ceramic is chosen, the imaginary part of the dielectric constant is relatively constant from one sintering bunch to another. However, the real part of the dielectric constant may scatter over a wide range. To ensure uniform quality of ceramic structures, ceramic makers perform sample tests to measure the dielectric properties of the material. However, these tests are destructive as they are based on removal of a portion of the ceramic structure. Moreover, the tested portion is generally small and at best yields a local value of the dielectric constant that is not representative of the ceramic structure as a whole.

BRIEF DESCRIPTION OF THE DRAWINGS

The embodiments of the present disclosure are illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIG. 5 illustrates a simplified circuit diagram representing various embodiments of test fixtures described herein;

FIG. 6 depicts a sectional view of a sample area of various embodiments of test fixtures described herein; and FIG. 7 illustrates a method for testing a sample in accordance with the various embodiments described herein.

DETAILED DESCRIPTION OF EMBODIMENTS

Figure 1:
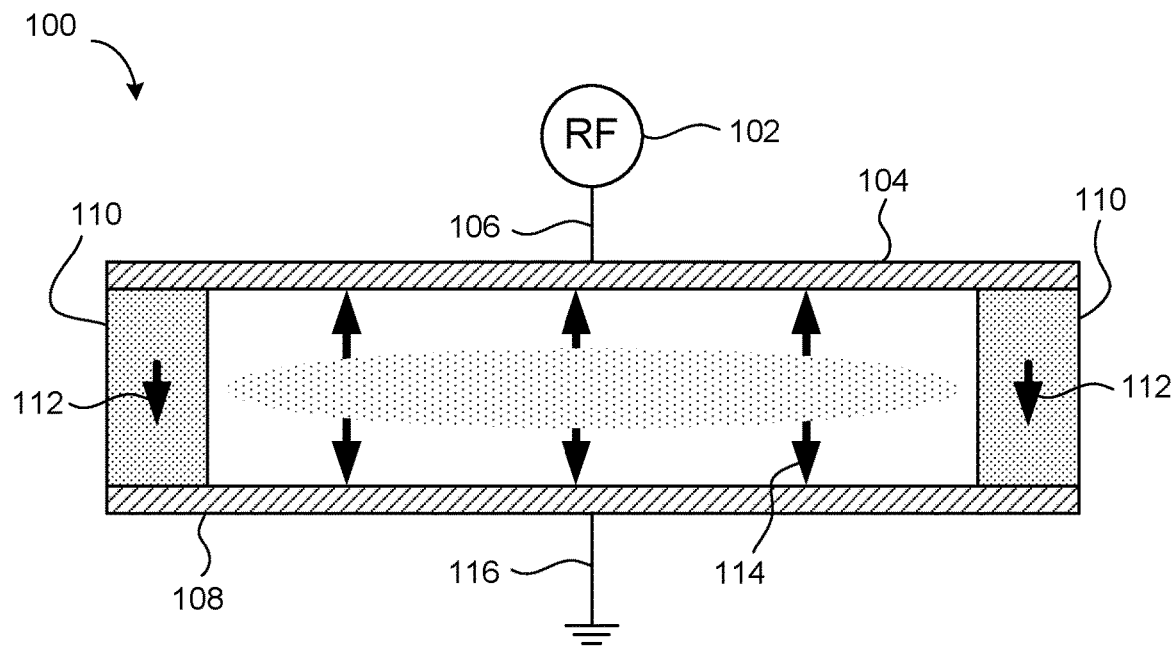
FIG. 1 depicts a sectional view of a plasma processing chamber.

Embodiments of the present disclosure provide a device for measuring one or more electrical properties of a structure, such as a ceramic ring. Such measured electrical properties may include a dielectric constant, a conductivity, an inductance, and so on. The device includes a test fixture with an inner conductor disposed within an outer conductor. The dimensions of the sidewalls of the inner and outer conductors are designed to match a characteristic impedance of an RF connector (e.g. of a coaxial connector). The embodiments described herein advantageously allow for averaging of the dielectric constant or other electrical properties over an entire structure, such as a ceramic ring or other chamber component for use in a plasma processing chamber, in a non-destructive fashion. For example, a whole ceramic ring may be placed into the test fixture and measured, rather than cutting a piece off of the ceramic ring and testing just that piece. Testing of the entire structure provides macro measurements that reflect values that are applicable in the actual processing environment in which the structure will be used. Moreover, the non-destructive test process enabled by the test fixture does not destroy or damage the chamber component or other structure that is tested.

In one aspect of the present disclosure, a test fixture includes an outer conductor having a base, a top, and an interior sidewall disposed between the base and the top. The test fixture further includes an inner conductor disposed within and electrically isolated from the outer conductor, the inner conductor including a top portion having a first diameter and a bottom portion having a second diameter such that the second diameter is greater than the first diameter. The test fixture further includes a sample area defined between the base of the outer conductor and the bottom portion of the inner conductor. The sample area is configured to receive a chamber component, and an electrical property of the chamber component is measurable based on application of a signal to at least one of the outer conductor or the inner conductor.

In one embodiment, the test fixture includes an RF connection site for connecting the test fixture to an RF connector such that a first electrical connection is made between the inner conductor and an interior conductive member of the RF connector and a second electrical connection is made between the outer conductor and an exterior conductive member of the RF connector. In one embodiment, an impedance of the inner conductor and the outer conductor is approximately matched to an impedance of the RF connector.

In one embodiment, the interior sidewall of the outer conductor defines a third diameter at the top of the outer conductor and a fourth diameter at the base of the outer conductor. In one embodiment, the interior sidewall is tapered such that the fourth diameter is greater than the third diameter. In one embodiment, a first ratio of the third diameter of the outer conductor to the first diameter of the inner conductor is about equal to a second ratio of the fourth diameter of the outer conductor to the second diameter of the inner conductor.

In one embodiment, an exterior sidewall of the inner conductor is tapered from the top portion of the inner conductor to the bottom portion of the inner conductor.

In one embodiment, the inner conductor includes a capacitor plate at the bottom portion. The second diameter corresponds to a diameter of the capacitor plate, and the sample area is defined between the base of the outer conductor and the capacitor plate. In one embodiment, the inner conductor further includes a third diameter near the capacitor plate that is less than the second diameter of the capacitor plate. The third diameter is greater than or equal to the first diameter.

In one embodiment, the top portion of the inner conductor protrudes from a top surface of the bottom portion of the inner conductor. In one embodiment, the outer conductor includes a lid disposed at the top of the outer conductor, the lid defining an opening through which a part of the top portion of the inner conductor passes through. In one embodiment, a first ratio of a diameter of the opening to the first diameter of the top portion of the inner conductor is about equal to a second ratio of a diameter of the interior sidewall of the outer conductor to the second diameter of the bottom portion of the inner conductor. In one embodiment, the top surface of the bottom portion of the inner conductor is about parallel to a bottom surface of the lid. In one embodiment, the top surface of the bottom portion of the inner conductor and the bottom surface of the lid define a space that is about equal to the diameter of the opening.

In one embodiment, the chamber component includes a ceramic ring having a diameter that is less than the second diameter.

In one embodiment, a diameter of the chamber component is less than the second diameter such that an edge effect between the chamber component and an outer edge of the bottom portion of the inner conductor is effectively independent of a material of the chamber component.

In one embodiment, the test fixture further includes a measuring device electrically coupled to the inner conductor and the outer conductor. The measuring device is configured to apply the signal to the at least one of the outer conductor or the inner conductor. In one embodiment, the measureable electrical property of the chamber component is an impedance, and the measuring device is configured to determine a dielectric constant of the chamber component based at least in part on the impedance.

In another aspect of the present disclosure, a system includes an outer conductor including a conductive housing and a conductive lid disposed above and in contact with the conductive housing, such that the conductive housing and the conductive lid define an interior region of the outer conductor. The system further includes an inner conductor disposed within the interior region of the outer conductor and electrically isolated from the outer conductor, the inner conductor including a top portion and a bottom portion. The top portion passes through an opening defined through the conductive lid, and the bottom portion includes a capacitor plate that is parallel to a bottom surface of the conductive housing.

In another aspect of the present disclosure, a method includes contacting a bottom surface of a test sample with a first surface of an outer conductor. The method further includes contacting a top surface of the test sample with a bottom portion of an inner conductor such that the inner conductor is disposed within and electrically isolated from the outer conductor. The inner conductor includes a top portion having a first diameter that is less than a second diameter of the bottom portion. The method further includes applying a signal between the inner conductor and the outer conductor, and measuring an impedance based on the applied signal. A dielectric constant of the test sample is computable from the measured impedance.

FIG. 1 depicts a sectional view of a plasma processing chamber 100. The plasma processing chamber 100 is referred to as a capacitively coupled plasma structure. A plasma is produced in the plasma processing chamber 100 by applying RF energy from an RF power source 102 to a suitable gas contained within the plasma processing chamber 100. Examples of processing gases that may be used to produce the plasma include silane, oxygen, dichlorosilane, and nitrous oxide. Other examples of processing gases include halogen containing gases such as $C_2F_6$, $SF_6$, $SiC_4$, HBr, $NF_3$, $CF_4$, $CHF_3$, $CH_2F_3$, $Cl_2$ and $SiF_4$, among others, and other gases such as $O_2$, or $N_2O$. Examples of carrier gases that may be used include $N_2$, He, Ar, and other gases inert to process gases (e.g. non-reactive gases). The gases may be introduced into plasma processing chamber 100 via one of a plurality of gas supply lines (not shown) once the chamber is sealed.

RF power source 102 is coupled to parallel plate electrodes 104 and 108 via an RF line 106. A return path 116 connects electrode 108 to ground. Sidewalls of the plasma processing chamber 100 are formed by the interior of ceramic ring 110. Power delivered to plasma processing chamber 100 from RF power source 102 is dissipated in the plasma as well as in ceramic ring 110. The power dissipation per unit volume of ceramic ring 110 is represented by:

$$P = \text{real}\left(\frac{1}{2}\vec{E} \cdot \frac{\partial \vec{D}}{\partial t}\right), \quad \text{Eq. 1}$$

where $\vec{D}=\in\vec{E}$, $\vec{E}$ is the applied electric field, $\in=|\in|\exp(j\in)$, $|\in|$ is the magnitude of the dielectric constant, and δ is the phase delay. A typical distribution of electric field in plasma sheaths is depicted as arrows 114, while that in the ceramic is depicted as arrows 112. The power dissipation in the ceramic ring is not negligible when $|\in|$ and δ have high values, such as >3 and >$10^{-3}$, respectively.

When measuring the dielectric constant of a small portion of a ceramic ring, such tests may measure local minima that are not representative of the average dielectric constant over the entire ceramic ring, which may be an underestimate of the dissipation inside the ceramic ring. On the other hand, such tests may measure local maxima that are also not representative of the average dielectric constant, leading to an overestimate of the dissipation inside the ceramic ring. Thus, in some instances it is useful to determine the average dielectric constant for the ceramic ring in order to account for local variations within the ceramic ring. Other statistical values of the dielectric constant such as the median dielectric constant may also be computed. For such purposes, an operator may often cut out many samples from a ceramic ring to perform measurements on each sample.

Note that some embodiments are described herein with regards to measuring a dielectric constant of a ceramic ring. However, it should be understood that embodiments also apply to measuring the dielectric constant of other structures, including other chamber components such as a ceramic lid, a single ring, an electrostatic puck, and so forth. Additionally, it should also be understood that embodiments may be used to measure values of electrical properties other than the dielectric constant. For example, the test fixtures described in embodiments herein may be used to compute average conductivity, average inductance, and so forth, for a structure.

Figure 2:
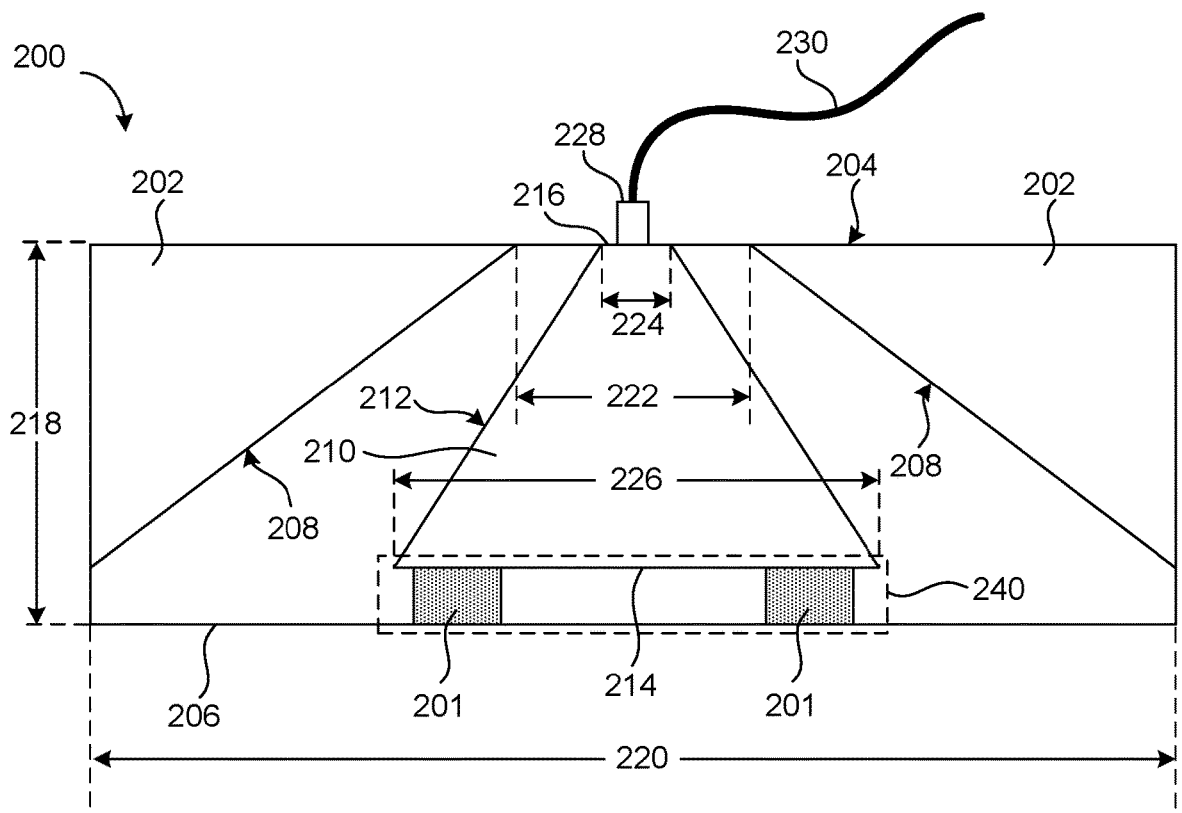
FIG. 2 depicts a sectional view of a first embodiment of a test fixture.

FIG. 2 depicts a sectional view of a first embodiment of a test fixture 200. Test fixture 200 may be used to test a ceramic ring and/or other chamber components. Test fixture 200 includes an outer conductor 202 and an inner conductor 210. A space between the outer conductor 202 and inner conductor 210 defines a receiving area 240 for a chamber component 201 that is to be tested. In some embodiments, chamber component 201 is centered within test fixture 200. Chamber component 201 is depicted as a ring structure, particularly a ceramic ring. However, it is to be understood that the ceramic ring is merely illustrative, and that the embodiments described herein are not limited to measuring electrical properties of ceramic rings. Any other suitable material or structure may also be tested. Moreover, structures to be tested are not limited to a ring structure, but may also be a disc, a square, a rectangle, an irregular shape, or any other suitable shape.

Outer conductor 202 includes base 206, which serves to support chamber component 201. Outer conductor 202 also has a top 204 and an interior sidewall 208 that surrounds inner conductor 210 and chamber component 201. Inner conductor 210 has an exterior sidewall 212, a bottom portion 214, and a top portion 216. Bottom portion 214 contacts chamber component 201, and may secure the chamber component 201 against base 206 of outer conductor 202. In some embodiments, a bottom surface of bottom portion 214 of inner conductor 210 may be flush with a top surface of chamber component 201 in some embodiments. In some embodiments, the bottom surface of bottom portion 214 of inner conductor 210 is flush with at least a portion of the top surface of chamber component 201.

Outer conductor 202 and inner conductor 210 are electrically isolated from each other. Outer conductor 202 and inner conductor 210 are connected to an RF connector 228 (e.g. a coaxial cable connector) at an RF connection site near top portion 216 of inner conductor 210 and top 204 of outer conductor 202. A first electrical connection is made between inner conductor 210 and an interior conductive member of RF connector 228 and a second electrical connection is made between outer conductor 202 and an exterior conductive member of RF connector 228. An electrical signal (e.g. an RF signal) may be applied to one or both of the inner conductor 210 and/or outer conductor 202 of test fixture 200. RF connector 228 may be connected to a measuring device (e.g. a network analyzer) via a coaxial cable 230. Alternatively, a different type of cable may be used. The measuring device may be configured to measure an electrical property of chamber component 201 (e.g. an impedance, a conductance, etc.).

RF connector 228 and coaxial cable 230 may have a characteristic impedance of 50Ω. Other cables may have other characteristic impedances. Coaxial cable 230 may be designed with different exterior-to-interior conductor ratios depending on the insulation used to separate the conductors. For example, if coaxial cable 230 uses air as an insulator, the ratio, α, between its exterior conductor diameter and its interior conductor diameter will be α=2.27. Alternatively, a value of α=3.21 may be exhibited when polytetrafluoroethylene (PTFE) is used as the insulator.

In order for a measuring device to measure the chamber component directly while minimizing reflection caused by the test fixture, the various embodiments of the test fixture described herein are exemplified as coaxial structures with multiple interior dimensions (e.g. interior diameters) designed to match the characteristic impedance of the measuring device and connector 228. As shown in FIG. 2, inner conductor 210 has a first diameter 224 at top portion 216 and a second diameter 226 at bottom portion 214. Outer conductor 202 has a third diameter 222 at top 204 and a fourth diameter 220 at base 206. Interior sidewall 208 of outer conductor 202 and exterior sidewall 212 of inner conductor 210 are designed so that a ratio of their respective diameters are matched at any point within test fixture 200. Specifically, a first ratio of third diameter 222 and first diameter 224 is about equal to a second ratio of fourth diameter 220 and second diameter 226. Similarly, a ratio of the diameter of the interior sidewall 208 to the diameter of the exterior sidewall 212 at a cross section taken at any given height within the test fixture 200 may be about the same.

In some embodiments, for example, when the characteristic impedance of the coaxial cable 230 is 50Ω, the first and second ratios are maintained at α=2.27 to have a characteristic impedance of 50 Ω with insulator of air. The ratios of diameters are dependent on the impedance to be matched, and thus α may be any suitable value. In the embodiments described herein, both outer conductor 202 and inner conductor 210 are depicted and described as being radially-symmetric about a center, in which their corresponding dimensions are referred to as "diameters." However, the embodiments described herein are not limited to radially-symmetric structures, and any suitable chamber shape that provides impedance matching may be used. For example, a square or rectangular chamber may be used. Thus, the term "diameter" used herein may refer generally to a dimension of a physical structure, such as a length or width.

In some embodiments, second diameter 226 may be greater than an outer diameter of chamber component 201 to produce an overhang. This design allows air within test fixture 200 to be present at the edge of the interface between inner conductor 210 and chamber component 201. The capacitor edge effect around bottom portion 214 is controlled strongly by the material occupying the very edge. Furthermore, an effective area/diameter of the capacitor is determined by this edge effect. In such embodiments, the material located at the very edge is air, keeping the effective area/diameter almost constant. An overhang of about 5-25 mm may be used in conjunction with any of the embodiments described herein.

In one example, in which test fixture 200 is used to measure a ceramic ring with an outer diameter on the order of 300-320 mm, first diameter 224 of inner conductor 210 is about 2 mm while chamber height 218 is on the order of 1 m. Such a design may be difficult to manufacture and costly, and thus modifications to the test fixture that help reduce the overall dimensions may be useful in some instances.

Figure 3:
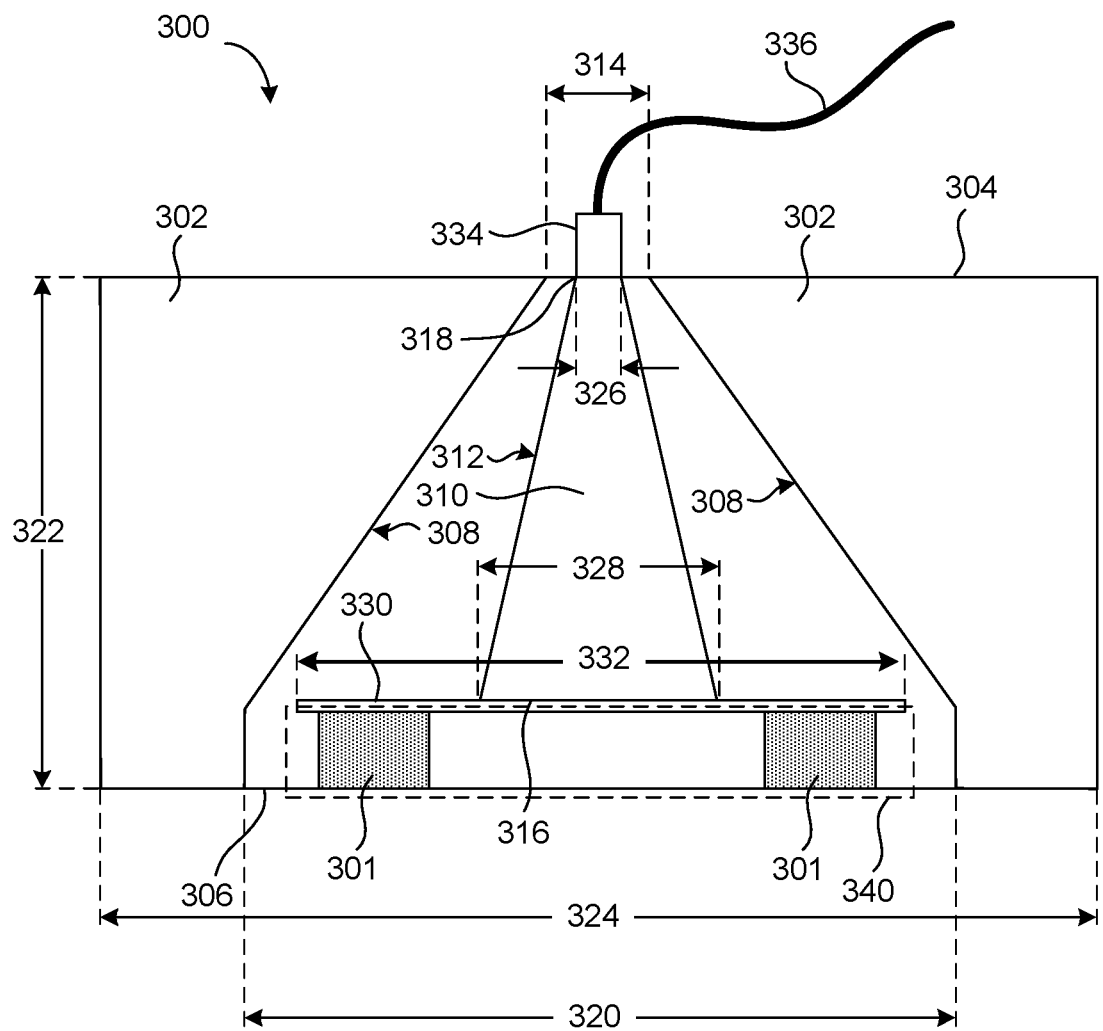
FIG. 3 depicts a sectional view of a second embodiment of a test fixture.

FIG. 3 depicts a sectional view of a second embodiment of a test fixture 300. Similar to test fixture 200, test fixture 300 includes an outer conductor 302 and an inner conductor 310, which together define a receiving area 340. Outer conductor 302 has an interior sidewall 308, a top portion 304, and a base 306 that supports chamber component 301 (which may be similar to chamber component 201 described with respect to FIG. 2). Inner conductor 310 has an exterior sidewall 312, a bottom portion 316, and a top portion 318. Similar to test fixture 200, in test fixture 300 an RF connector 334 connects inner conductor 310 and outer conductor 302 to a measuring device (e.g. a network analyzer) via coaxial cable 336 or other cable.

Test fixture 300 also includes a capacitor plate 330 that contacts a top surface of chamber component 301. By making capacitor plate 330 thin (e.g. 5-15 mm), the overall dimensions of test fixture 300 can be designed to be smaller than those of test fixture 200. In one embodiment, inner conductor 310 may be a separate component from capacitor plate 330 that interfaces with a top surface of capacitor plate 330 at bottom portion 316. In another embodiment, capacitor plate 330 and inner conductor 310 may together form a single contiguous component. In each of these embodiments, inner conductor 310 and capacitor plate 330 may be referred to collectively as the "inner conductor", and capacitor plate 330 may be considered to be a part of the inner conductor.

Inner conductor 310 has a first diameter 326 at top portion 318, a second diameter 332 corresponding to the diameter of capacitor plate 330, and a third diameter 328 at bottom portion 316. Outer conductor 302 has a fourth diameter 314 at top portion 304 and a fifth diameter 320 at base 306. As in test fixture 200, a first ratio of fourth diameter 314 to first diameter 326 is about equal to a second ratio of fifth diameter 320 to third diameter 328, and these ratios are defined as α so as to match the characteristic impedance, $Z_c$, of the RF connector 334 and coaxial cable 336 (e.g. α=2.27, if $Z_c$=50Ω). As a result of utilizing capacitor plate 330, third diameter 328 may be reduced to less than an inner diameter of chamber component 301 (e.g. a ceramic ring with an outer an inner diameter). Chamber width 324 of test fixture 300 may be comparable to or less than a width of test fixture 200. Additionally, chamber height 322 may be on the order of 300-500 mm, and thus significantly smaller than chamber height 218 of test fixture 200.

Figure 4A:
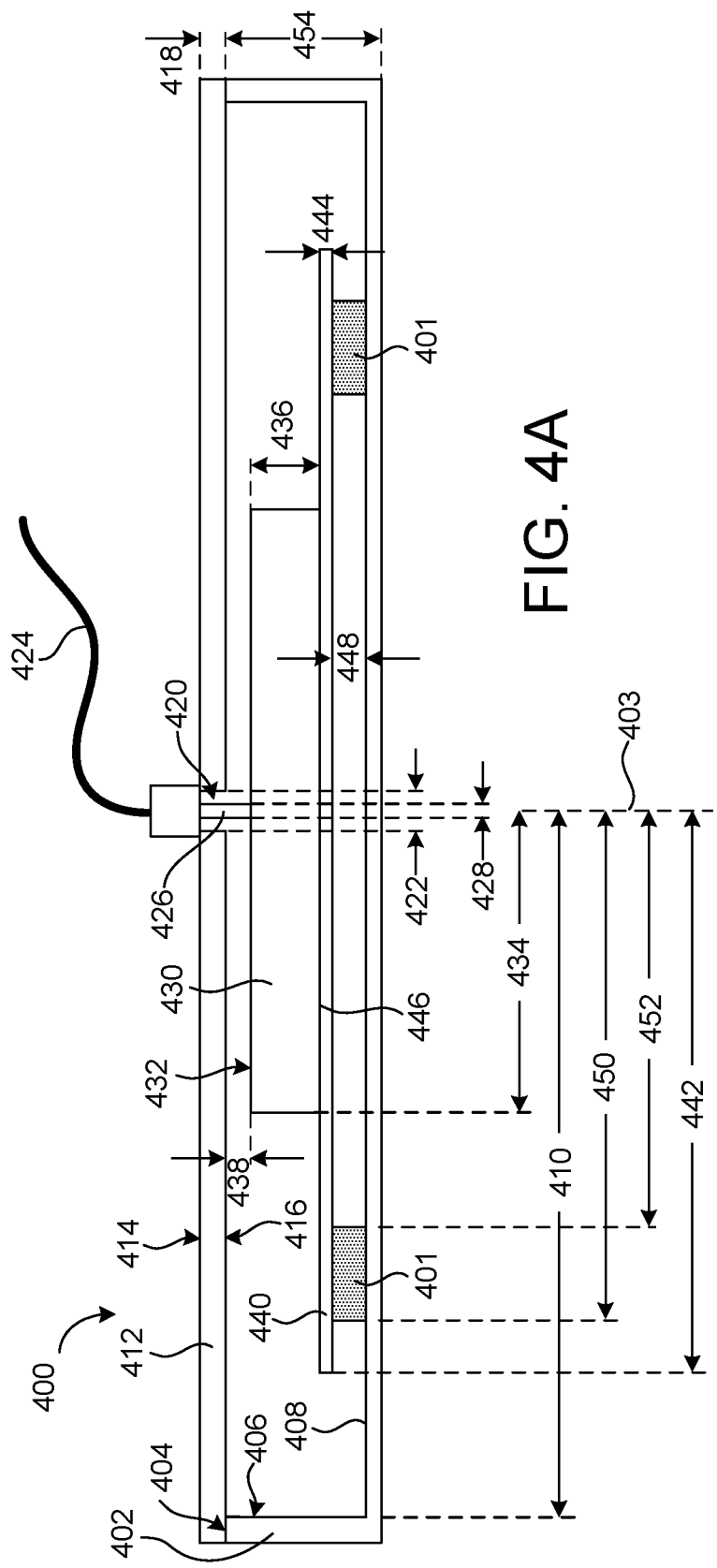
FIG. 4A depicts a sectional view of a third embodiment of a test fixture.

FIG. 4A depicts a sectional view of a third embodiment of a test fixture 400. Test fixture 400 is designed to reduce a chamber height 454 of test fixture 400 to a smaller size (e.g. on the order of 80-100 mm) than the heights of test fixtures 200 and 300, while still performing the same function as test fixtures 200 and 300. This can be achieved by using a design that leverages a shunt capacitance to connect two inner conductors with largely different diameters.

Test fixture 400 includes an outer conductor 402 that has an interior sidewall 406 and a base 408. As depicted, the interior sidewall 406 may be vertical or approximately vertical. Alternatively, the interior sidewall may have a slope. The outer conductor may further include (or electrically couple to) a lid 412, which may be supported at an interface 404 by sidewalls of the outer conductor 402. Lid 412 may have a thickness 418 of about 4-10 mm (e.g. of 6 mm in one embodiment). Interior sidewall 406 may have a height (from base 408 to the bottom surface 416 of lid 412) that is less than 100 mm. In a further embodiment, interior sidewall 406 has a height about 70-80 mm (e.g. of about 75.5 mm in one embodiment). In some embodiments, lid 412 is a separate, removable lid that interfaces with outer conductor 402. In other embodiments, lid 412 and outer conductor 402 may form a single contiguous component. Base 408 may have a radius 410 that is dependent on a size of a structure or structures that will be measured by the test fixture 400. In one embodiment, the base 408 has a radius 410 of approximately 250-350 mm (e.g. 292 mm in one embodiment) relative to a central axis 403. However, the base 408 may also have other radiuses.

To load chamber component 401 into test fixture 400, an entry port may be utilized in test fixture 400 to introduce chamber component 401 through interior sidewall 406. In some embodiments, base 408 may be detachable from outer conductor 402. Alternatively the lid 412 may be opened to insert the chamber component 401. In each of these embodiments, outer conductor 402, lid 412, and base 408 may be referred to collectively as the "outer conductor."

Similar to test fixture 300, test fixture 400 includes an inner conductor 430 that includes a capacitor plate 440 located at a bottom portion 446 of inner conductor 430. A bottom surface of capacitor plate 440 contacts a top surface of chamber component 401. Capacitor plate 440 may have a thickness 444 of 5-20 mm, and a radius 442 of 80-180 mm relative to central axis 403. Chamber component 401 may have outer radius 450 of 70-150 mm and an inner radius 452 of 10-100 mm (depending on outer radius 450) relative to central axis 403, and capacitor plate 440 overhangs chamber component 401 by about 1-30 mm to effectively eliminate sample edge effects. The receiving area height 448 depends on a thickness of chamber component 401. RF connector 423 interfaces with a top surface 414 of lid 412 and a top portion 426 of inner conductor 430, and connects test fixture 400 to a measuring device via coaxial cable 424 or other cable.

Inner conductor 430 is designed to have discrete regions of differing diameter, in contrast to the tapered structures of inner conductors 210 and 310 of FIGS. 2 and 3, respectively. Inner conductor 430 in one embodiment includes a top portion 426, bottom portion 446, and capacitor plate 440. Top portion 426 has a diameter 428 (e.g. 7.7 mm) and a height that may be about equal to thickness 418 of lid 412. Bottom portion 446 may have a thickness 436 of 30-50 mm (e.g. 37 mm in one embodiment) and a radius 434 of 50-70 mm (e.g. 64 mm in one embodiment). Top portion 426, bottom portion 446, and capacitor plate 440 may be individual components, contiguous, or a combination thereof. Each of top portion 426, bottom portion 446, and capacitor plate 440 may be referred to collectively as the "inner conductor."

A part of top portion 426 of inner conductor 430 may protrude vertically from top surface 432 of inner conductor, and pass through opening 420 of lid 412 to make an electrical connection with RF connector 423. A first ratio of diameter 422 of opening 420 to radius 434 of top portion 426 is about equal to a second ratio of radius 410 of outer conductor 402 to radius 434 of bottom portion 446. As discussed above, spacing 438 between top surface 432 of inner conductor 430 and a bottom surface 416 of lid 412 introduces a shunt capacitance between grounded lid 412 and inner conductor 430. Spacing 438 may be selected to add a specific shunt capacitance (e.g. impedance of 333Ω in one embodiment) that is large enough to act as a buffer to the applied signal while introducing a small perturbation. This buffering effect allows for chamber height 454 to be relatively small compared to chamber heights 218 and 322. Chamber height 454 may be selected to allow for a suitable thickness 436 of inner conductor 430 such that thickness 436 is at least 2-3 times greater than thickness 444 of capacitor plate 440.

Figure 4B:
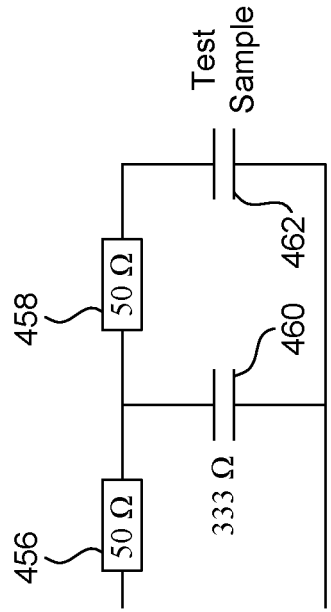
FIG. 4B depicts a circuit schematic of the third embodiment of a test fixture.

FIG. 4B depicts a circuit schematic of the third embodiment of a test fixture. The first ratio of diameter 422 to diameter 428 is represented by impedance 456 (e.g. 50Ω), and the second ratio of radius 410 to radius 434 is represented by impedance 458 (e.g. 50Ω). Spacing 438 introduces a shunt capacitance 460 having a larger impedance than impedances 456 and 458 (e.g. 333Ω). Chamber component 401 is represented by test sample capacitance 462.

FIG. 5 illustrates a simplified circuit diagram of a system 600 representing the various embodiments of test fixtures described herein. System 600 is a model used for calibration, and is represented by test fixture 602 and test sample 604. In general, calibration may be helpful for ceramic ring samples when the ceramic material has a small loss tangent on the order of $10^{-4}$. In system 600, test sample 604 has an impedance represented by $Z_{in}$. The overall impedance 606 of test fixture 602 and test sample 604, namely $Z_{out}$, is related to the sample impedance by:

$$Z_{in} = \frac{AZ_{out} + B}{CZ_{out} + D}, \quad \text{Eq. 2}$$

where A, B, C, and D are calibration parameters that can be determined from multivariable analysis of three or more samples.

FIG. 6 depicts a sectional view of a sample area of the various embodiments of test fixtures described herein. Section 650 represents the sample areas of test fixtures 200, 300, and 400. Ceramic ring 651 is located between a bottom surface of inner conductor 652 and a base of outer conductor 654, and is centered around central axis 656. Note that in alternative embodiments the ceramic ring 651 or other tested structure may not be centered. The sample area has an overall radius 662 (represented by an effective radius $R_{out}$ which takes into account a capacitor edge effect). Ceramic ring 651 has an inner diameter 658 and an outer diameter 660 (represented by $R_{in}$ and $R_{mid}$, respectively). The capacitance of the ceramic ring is given by:

$$C = \frac{\varepsilon_0 \pi R_{in}^2}{d} + \frac{\varepsilon_0 \varepsilon_{cer} \pi (R_{mid}^2 - R_{in}^2)}{d} + \frac{\varepsilon_0 \pi (R_{out}^2 - R_{mid}^2)}{d}, \quad \text{Eq. 3}$$

where $\in_{cer}$ is the complex valued dielectric constant of ceramic ring 651, and the impedance of ceramic ring 651 is given by:

$$Z_{in} = \frac{1}{j\omega C}. \quad \text{Eq. 4}$$

Tables 1-3 contain calibration data for an exemplary test device.

TABLE 1

Calibration samples and relevant experimental parameters

| Calibration Sample | $Z_{out}$ (Ω) | ε or $Z_{in}$ (if known) | tan δ |
|---|---|---|---|
| Aluminum disc | 0.010 + j1.458 | $Z_{in}$ = 0.35 Ω | N/A |
| Plastic disc | 0.054 – j20.971 | ε = 3.3 – j0.0851 | 0.00258 |
| Plastic ring | 0.033 – j32.141 | ε = 3.3 – j0.0851 | 0.00258 |

In Table 1, three different calibration samples were used: an aluminum disc, a plastic disc, and a plastic ring. The impedance of the aluminum disc and the dielectric constants for the plastic disc and ring were previously known. Using the test device shown in FIGS. 5 and 6, $Z_{out}$ for each of the calibration samples was then measured using a network analyzer.

TABLE 2

Calibration parameters

| A | B | C | D |
|---|---|---|---|
| 14.1 + j150 | –216 + j74.8 | 1 | 8.96 + j141 |

Multivariable analysis was used to obtain each of the calibration parameters A, B, C, and D, as shown in Table 2.

TABLE 3

Calculated dielectric constants for different samples

| Sample | $Z_{out}$ (Ω) | $\varepsilon_{cer}$ (calculated) | Loss tangent |
|---|---|---|---|
| Ceramic 1 | –0.093 – j17.483 | 9.7 – 0.006 | 6.2e–4 |
| Ceramic 2 | –0.005 – j17.422 | 9.7 – j0.001 | 11e–4 |
| Ceramic 3 | 0.285 – j17.098 | 10 – j0.270 | 265e–4 |

Using the data of Table 2, $Z_{out}$ was measured for three different ceramic rings, as shown in Table 3. It is noted that some of the real parts of $Z_{out}$ appear to be negative, which may have been caused by imperfect calibration of the network analyzer for small loss tangents. However, the correction for the imperfect calibration is implicitly included in the calibration process of A, B, C, and D. Hence, these negative real part of $Z_{out}$ may then be transformed by Eq. 2 to the positive real parts of $Z_{in}$. Finally, $\in_{cer}$ may be determined by Eqs. 3 and 4 for each of three ceramic rings, which show good agreement with those of small samples measured by a commercial RF impedance analyzer.

FIG. 7 illustrates a process 700 for testing a sample in accordance with the various embodiments described herein. In one embodiment, process 700 for using a test fixture (e.g. test fixtures 200, 300, and 400) to measure electrical properties of test samples begins at block 702. At block 704, the test sample (e.g. chamber components 201, 301, or 401: a ceramic ring, ceramic disc, plastic ring, plastic disc, or any other suitable material for which the dielectric constant is to be measured) is loaded onto a bottom surface of an outer conductor housing (e.g. bases 206, 306, and 408). The outer conductor housing (e.g. outer conductors 202, 302, and 402) may be contained within an insulated housing, or may be a standalone structure. In some embodiments, the test fixture may be in the form of a test chamber and may be part of a larger test device that includes a built-in test apparatus for performing electrical measurements. The test fixture may also be a standalone test fixture that is configured to interface with a test apparatus (e.g. a network analyzer). The user may manually load the test sample into the outer conductor housing. In one embodiment, the test fixture may be part of an automated system that automatically places the test sample into the chamber. For example, the tests may be executed in a high-throughput fashion using a robotically-automated loading system that loads and unloads multiple test samples in between measurements. In one embodiment, the outer conductor housing may include fiducial marks to indicate where the test sample should be placed. In another embodiment, the outer conductor housing may include a slot or raised tabs that confine the test sample to a particular location of the outer conductor housing. In another embodiment, centering pieces may be placed inside the outer conductor housing around the test sample to center the sample. The test samples may be removed prior to testing.

After the test sample is loaded, the process proceeds to block 706. In block 706, a bottom surface of an inner conductor (e.g. inner conductors 210, 310, and 430) is contacted with a top surface of the test sample. For example, the contact between the inner conductor and the test sample may be made manually or automatically, as described above. In some embodiments, a lid (e.g. lid 412) may be placed over the outer conductor housing to close the test fixture. An electrical connection may be made between the inner conductor and outer conductor by connecting an electrical connector (e.g. RF connectors 228, 334, and 423) to a connection site on top of the test device. The electrical connector is connected to a measurement device (e.g. a network analyzer) for performing electrical measurements.

After the inner conductor is placed on top of the test sample, the process proceeds to block 708. At block 708, an electrical signal (e.g. an RF signal of a frequency ranging from 1-100 MHz) is applied between the inner conductor and the outer conductor housing. In some embodiments, the electrical signal may be delivered to the inner conductor directly while the outer conductor housing is grounded. An impedance of the system is measured by the measurement device, which may measure the impedance of the test sample alone while minimizing reflections caused by an unmatched impedance of the test device.

After applying the RF signal between the inner conductor and the outer conductor housing, the process proceeds to block 710. At block 710, an average dielectric constant for the test sample is computed based on the measured impedance. In some embodiments, the measurement device may compute the dielectric constant based on the measured impedance, or the impedance data may be passed on to a separate workstation (e.g. a computing terminal, a laptop, a mobile device, etc.) that performs the computation. In some embodiments, the dielectric constant may be computed based on previously acquired calibration data obtained from different calibration samples. If the test device is part of an automated system, each of the calibration samples may be automatically measured in series, followed by a measurement of the test sample after the system has been calibrated. The process ends at block 712.

Although the operations of the methods described herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the embodiments of the present disclosure. Thus, the specific details set forth are merely exemplary. Particular implementations may vary from these exemplary details and still be contemplated to be within the scope of the present disclosure.

Reference throughout this specification to "one embodiment", "some embodiments", "certain embodiments", or "an embodiment" indicates that a particular feature, structure, or characteristic described in connection with the embodiment is included in at least one embodiment. Thus, the appearances of the phrase "in one embodiment", "in some embodiments", "in certain embodiments", or "in an embodiment" in various places throughout this specification are not necessarily all referring to the same embodiment. In addition, the term "or" is intended to be an inclusive "or" rather than an exclusive "or." When the term "about" or "approximately" is used herein, this is intended to indicate that the nominal value presented is precise within ±10%.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A test fixture comprising:
an outer conductor; and
an inner conductor disposed within and electrically isolated from the outer conductor, wherein the inner conductor comprises a top portion having a first diameter, a bottom portion having a second diameter, and a third portion proximate the bottom portion that has a third diameter that is less than the second diameter and is greater than the first diameter, wherein an electrical property of a chamber component disposed within the outer conductor is measurable based on application of a signal to at least one of the outer conductor or the inner conductor.

2. The test fixture of claim 1, wherein the top portion of the inner conductor protrudes vertically from a top surface of the third portion of the inner conductor, wherein the top portion of the inner conductor passes through an opening in a lid of the outer conductor to make an electrical connection with an RF connector.

3. The test fixture of claim 1, wherein the outer conductor comprises a lid, wherein a first ratio of a fourth diameter of an opening in the lid to the first diameter of the inner conductor is substantially equal to a second ratio of a fifth diameter of an inner sidewall of the outer conductor to the second diameter of the bottom portion.

4. The test fixture of claim 1, wherein the bottom portion comprises a capacitor plate, wherein a bottom surface of the capacitor plate is to contact an upper surface of the chamber component disposed within the outer conductor.

5. The test fixture of claim 4, wherein an outer diameter of the chamber component is less than the second diameter such that the capacitor plate overhangs the chamber component to effectively eliminate sample edge effects between the chamber component and an outer edge of the capacitor plate.

6. The test fixture of claim 1, wherein a radio frequency (RF) connector interfaces with a top surface of a lid of the outer conductor and the top portion of the inner conductor, wherein the RF connector couples the test fixture to a measuring device.

7. The test fixture of claim 1, wherein the signal is applied between the inner conductor and the outer conductor, and wherein spacing between an upper surface of the third portion and a lower surface of a lid of the outer conductor provides a specific shunt capacitance that acts as a buffer to the signal.

8. A system comprising:
an outer conductor;
an inner conductor disposed within and electrically isolated from the outer conductor; and
a radio-frequency (RF) connection site to connect the outer conductor and the inner conductor to an RF connector, wherein a first electrical connection is to be made between the inner conductor and an interior conductive member of the RF connector and a second electrical connection is to be made between the outer conductor and an exterior conductive member of the RF connector, wherein an electrical property of a chamber component disposed within the outer conductor is measurable based on application of a signal to at least one of the outer conductor or the inner conductor.

9. The system of claim 8, wherein a top portion of the inner conductor passes through an opening in a lid of the outer conductor to make the first electrical connection with the interior conductive member of the RF connector.

10. The system of claim 8, wherein the outer conductor comprises a lid, wherein a first ratio of a fourth diameter of an opening in the lid to a first diameter of a top portion of the inner conductor is substantially equal to a second ratio of a fifth diameter of an inner sidewall of the outer conductor to a second diameter of a bottom portion of the inner conductor.

11. The system of claim 8, wherein a bottom portion of the inner conductor comprises a capacitor plate, wherein a bottom surface of the capacitor plate is to contact an upper surface of the chamber component disposed within the outer conductor.

12. The system of claim 11, wherein an outer diameter of the chamber component is less than a second diameter of the bottom portion of the inner conductor such that the capacitor plate overhangs the chamber component to effectively eliminate sample edge effects between the chamber component and an outer edge of the capacitor plate.

13. The system of claim 8, wherein the system comprises a test fixture comprising the outer conductor and the inner conductor, wherein the RF connector couples the test fixture to a measuring device.

14. The system of claim 8, wherein the inner conductor comprises a top portion having a first diameter, a bottom portion having a second diameter, and a third portion proximate the bottom portion that has a third diameter that is less than the second diameter and is greater than the first diameter.

15. A method comprising:
placing a test sample within an outer conductor, wherein an inner conductor is disposed within and electrically isolated from the outer conductor, the inner conductor comprising a top portion and a bottom portion, the top portion having a first diameter that is less than a second diameter of the bottom portion, wherein a diameter of the test sample is less than the second diameter, wherein an edge effect between the test sample and an outer edge of the bottom portion of the inner conductor is effectively independent of a material of the test sample; and
measuring an impedance based on a signal applied between the inner conductor and the outer conductor.

16. The method of claim 15, wherein a lid of the outer conductor comprises an opening, wherein a first ratio of a third diameter of the opening to the first diameter of the top portion of the inner conductor is substantially equal to a second ratio of a fourth diameter of an interior sidewall of the outer conductor to the second diameter of the bottom portion of the inner conductor.

17. The method of claim 15, wherein a top surface of the bottom portion of the inner conductor and a bottom surface of a lid of the outer conductor define a space, wherein the space is substantially equal to the diameter of an opening in the lid through which the top portion of the inner conductor extends.

18. The method of claim 15 further comprising computing an average dielectric constant of the test sample based on the measured impedance.

19. The method of claim 15 further comprising contacting a bottom surface of the bottom portion of the inner conductor on a top surface of the test sample.

20. The method of claim 15, wherein the inner conductor comprises a third portion proximate the bottom portion that has a third diameter that is less than the second diameter and is greater than the first diameter.

* * * * *